United States Patent
Baucom et al.

(10) Patent No.: US 9,446,257 B2
(45) Date of Patent: Sep. 20, 2016

(54) AUTOMATED EXTERNAL DEFIBRILLATOR SUPPORT MECHANISM

(71) Applicant: ZOLL Medical Corporation, Chelmsford, MA (US)

(72) Inventors: Allan Scott Baucom, Boxboro, MA (US); George Reilly, Chelmsford, MA (US); Peter A. Lund, Nashua, NH (US); Darlene Justesen, Beverly, MA (US); Melissa M. Dascoli, Wakefield, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 14/624,876

(22) Filed: Feb. 18, 2015

(65) Prior Publication Data
US 2015/0231404 A1  Aug. 20, 2015

Related U.S. Application Data

(60) Provisional application No. 61/941,292, filed on Feb. 18, 2014.

(51) Int. Cl.
*A61N 1/39* (2006.01)

(52) U.S. Cl.
CPC .................. *A61N 1/3993* (2013.01)

(58) Field of Classification Search
CPC ............... F16M 11/04; F16M 11/105; A45C 2200/15; A61N 1/3993
See application file for complete search history.

(56) References Cited

U.S. PATENT DOCUMENTS

| | | | |
|---|---|---|---|
| 6,422,669 B1* | 7/2002 | Salvatori | A61N 1/3968 206/320 |
| 8,726,439 B2* | 5/2014 | Orzeck | B25F 1/003 248/126 |
| 2003/0167074 A1 | 9/2003 | Merry | |
| 2003/0208237 A1 | 11/2003 | Locke et al. | |
| 2013/0002049 A1* | 1/2013 | Stampfli | H01M 2/1022 307/150 |

FOREIGN PATENT DOCUMENTS

WO   WO2011/066566   6/2011

OTHER PUBLICATIONS

European Search Report, 15155666.9, Jul. 15, 2015, 6 pages.

* cited by examiner

*Primary Examiner* — Amanda Patton
(74) *Attorney, Agent, or Firm* — Fish & Richardson P.C.

(57) ABSTRACT

According to an embodiment of the present invention, an apparatus includes an automated external defibrillator including at least one display. The apparatus also includes a support mechanism for supporting the automated external defibrillator. The support mechanism includes a stand connected to a hinge that is connected to the automated external defibrillator. The hinge is capable of placing the stand in a deployed position for supporting the automated external defibrillator during operation and is capable of placing the stand in a stowed position for storing the automated external defibrillator.

18 Claims, 5 Drawing Sheets

AUTOMATED EXTERNAL DEFIBRILLATOR SUPPORT MECHANISM

CLAIM OF PRIORITY

This application claims priority under 35 USC §119(e) to U.S. Patent Application Ser. No. 61/941,292, filed on Feb. 18, 2014 the entire contents of which are hereby incorporated by reference.

TECHNICAL FIELD

The invention relates generally to a support mechanism for a portable defibrillator such as a stand for an automated external defibrillator (AED).

BACKGROUND

Sudden health problems such as sudden cardiac arrest and injuries caused by accidents kill thousands of people and cause permanent injury every year. Fast and competent care to resuscitate such victims of these problems can be essential to positive outcomes in such situations. For example, it is said that the chance of surviving a sudden cardiac arrest falls by ten percent for every minute of delay in providing effective treatment.

Resuscitation treatments for patients suffering from cardiac arrest generally include clearing and opening the patient's airway, providing rescue breathing for the patient, and applying chest compressions to provide blood flow to the victim's heart, brain, and other vital organs. If the patient has a shockable heart rhythm (ventricular fibrillation or pulseless ventricular tachycardia), resuscitation also may include defibrillation therapy using an AED, for example. Along with such action, an electrocardiogram (ECG) signal for the patient may be electronically captured, displayed, and monitored, so that rescuers can determine when the patient's heart has returned to normal or near-normal operation, and determine when the heart exhibits a shockable rhythm. About half of patients who suffer ventricular fibrillation (VF) have a recurrence of VF within minutes of successful VF conversion, which may then require reconversion. Patient odds of survival fall with repeated VF recurrence during resuscitation.

Survivability of a cardiac arrest patient may often depend being able to efficiently deploy an AED for use during an emergency. Similar to other types of emergency equipment used in these situations, reducing the time needed to deploy the equipment may factor into the successful treatment of the patient. Valuable time may be further lost as an AED is positioned in a less-than-optimum environment (e.g., harsh terrain and weather, stressful conditions, etc.), during which the emergency personnel could have been treating the patient with the AED.

SUMMARY

In one aspect, an apparatus includes an automated external defibrillator that includes at least one display. The apparatus also includes a support mechanism for supporting the automated external defibrillator. The support mechanism includes a stand connected to a hinge that is connected to the automated external defibrillator. The hinge is capable of placing the stand in a deployed position for supporting the automated external defibrillator during operation and is capable of placing the stand in a stowed position for storing the automated external defibrillator.

The aforementioned apparatus, wherein a first angle is formed between the stand and the automated external defibrillator when in the deployed position.

The aforementioned apparatus, wherein a second angle is formed between the stand and the automated external defibrillator when in the stowed position.

The aforementioned apparatus, wherein the first angle is larger than the second angle.

The aforementioned apparatus, wherein the hinge places the stand in the deployed position absent an external force being applied to the stand.

The aforementioned apparatus, wherein the hinge places the stand in the stowed position when an external force is applied to the stand.

The aforementioned apparatus, wherein the stand is configured to receive the external force from a portion of a storage container.

The aforementioned apparatus, wherein the hinge is spring loaded and places the stand in the stowed position absent an external forces being applied to the stand.

The aforementioned apparatus, wherein the hinge is spring-loaded and places the stand in the deployed position when an external force is applied to the stand.

The aforementioned apparatus, wherein the hinge is spring-loaded and places the stand in the stowed position when the apparatus is placed on its back.

In another aspect, an apparatus includes an automated external defibrillator including at least one display. The apparatus also includes a support mechanism for supporting the automated external defibrillator that includes a stand capable of assisting the supporting of the automated external defibrillator during operation. The support mechanism also includes a spring-loaded hinge that is connected to the stand and the automated external defibrillator. The spring-loaded hinge is capable of placing the stand in a deployed position for supporting the automated external defibrillator during operation and is also capable of placing the stand in a stowed position for storing the automated external defibrillator. The spring-loaded hinge places the stand in the deployed position absent an external force being applied to the stand.

The aforementioned apparatus, wherein a first angle is formed between the stand and the automated external defibrillator when in the deployed position.

The aforementioned apparatus, wherein a second angle is formed between the stand and the automated external defibrillator when in the stowed position.

The aforementioned apparatus, wherein the first angle is larger than the second angle.

The aforementioned apparatus, wherein the spring-loaded hinge places the stand in the stowed position when the apparatus is placed on its back.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
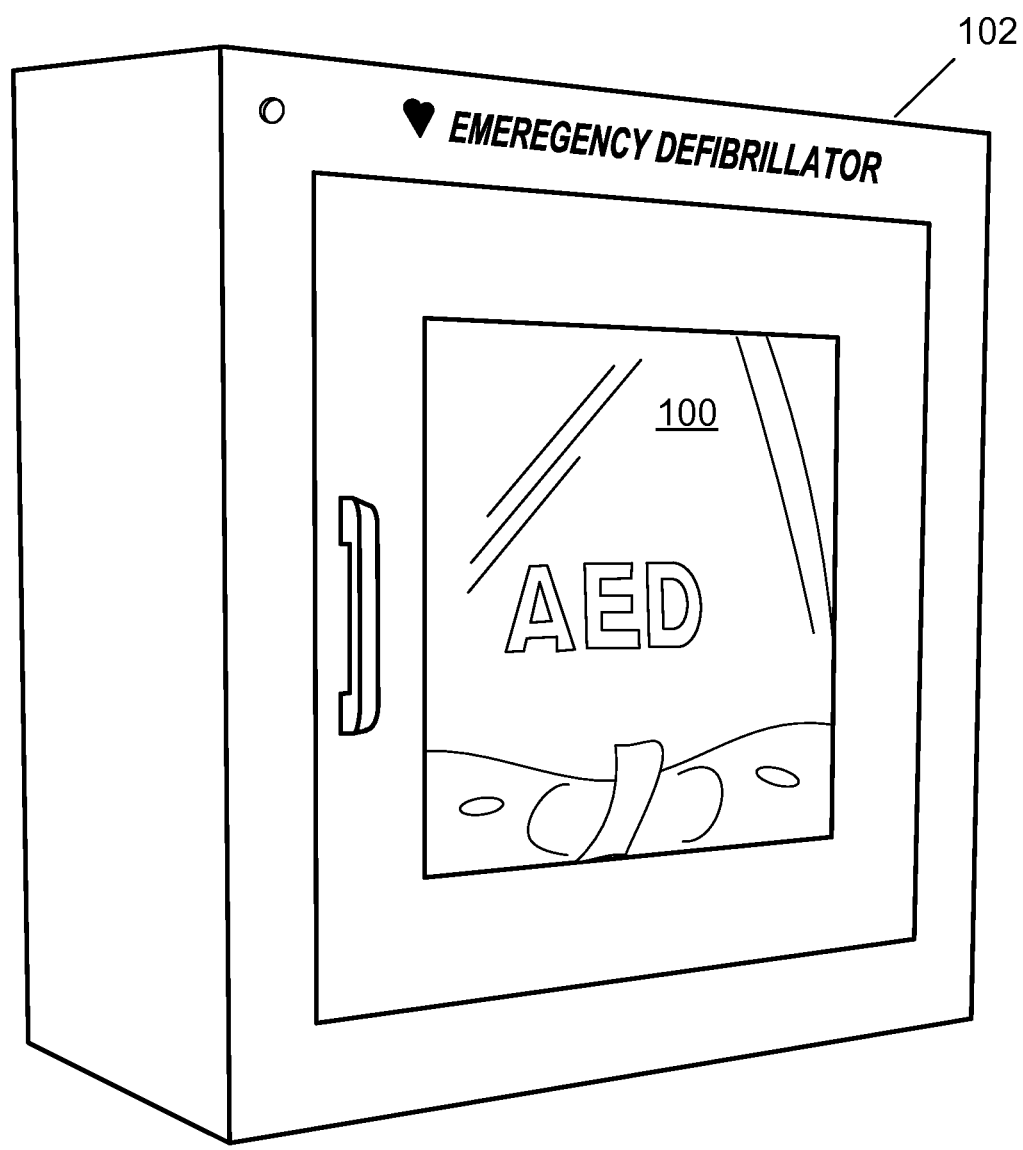
FIG. 1 illustrates an AED stowed in an accessible wall cabinet.
Figure 2B:
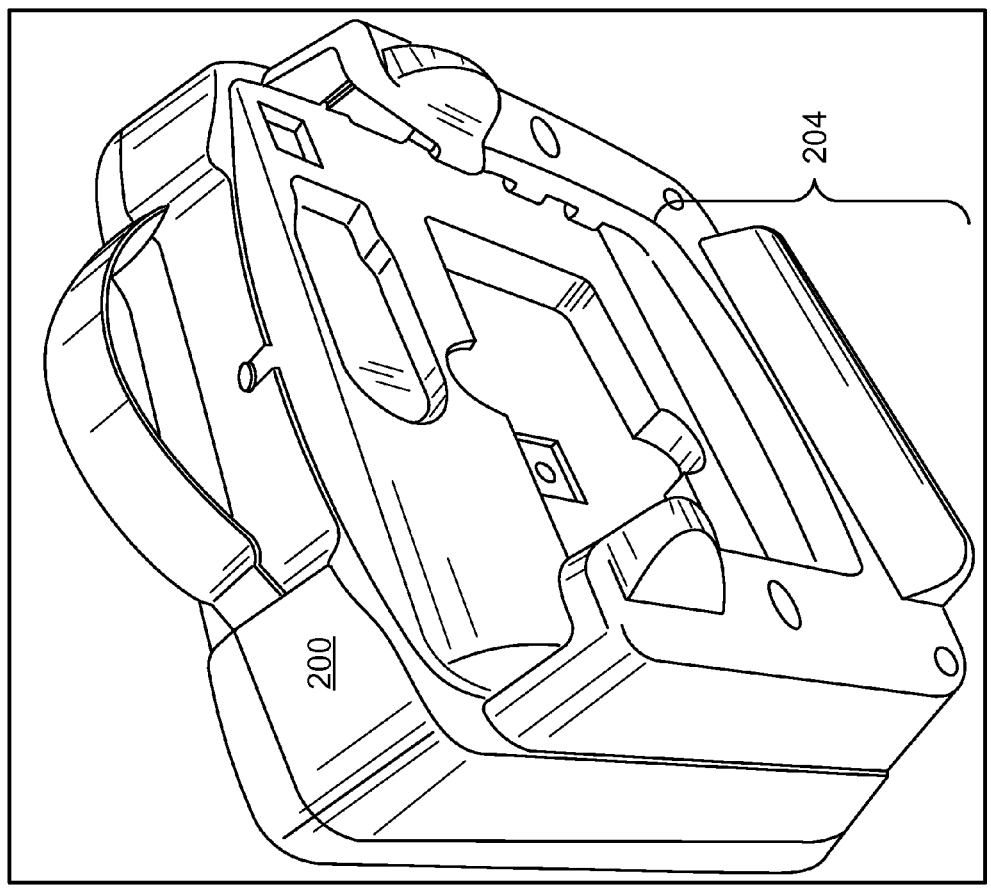
FIG. 2(a)-(d) illustrates the AED with a stand deployed and stowed to provide support assistance.
Figure 2A:
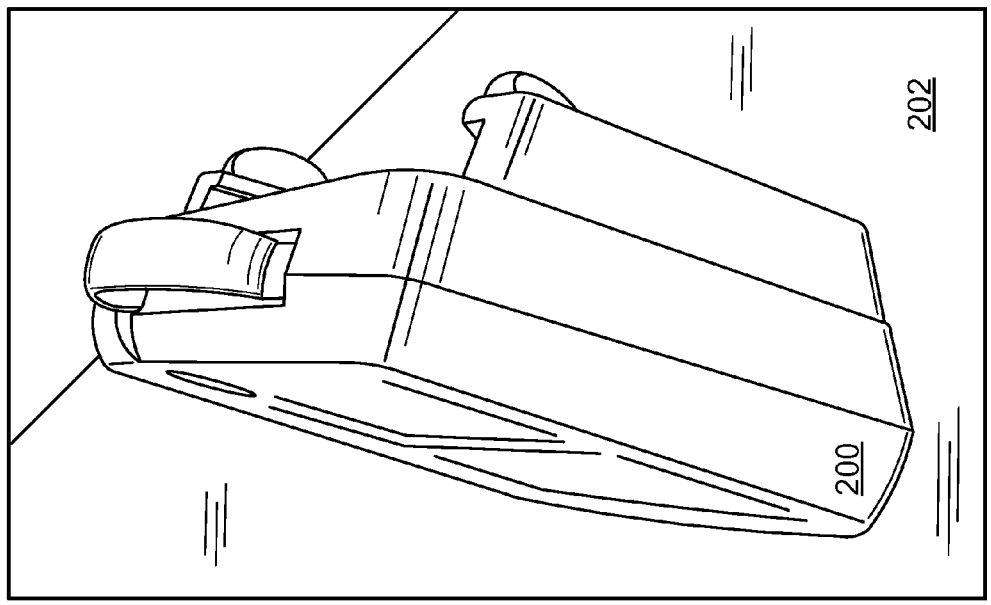
Figure 2C:
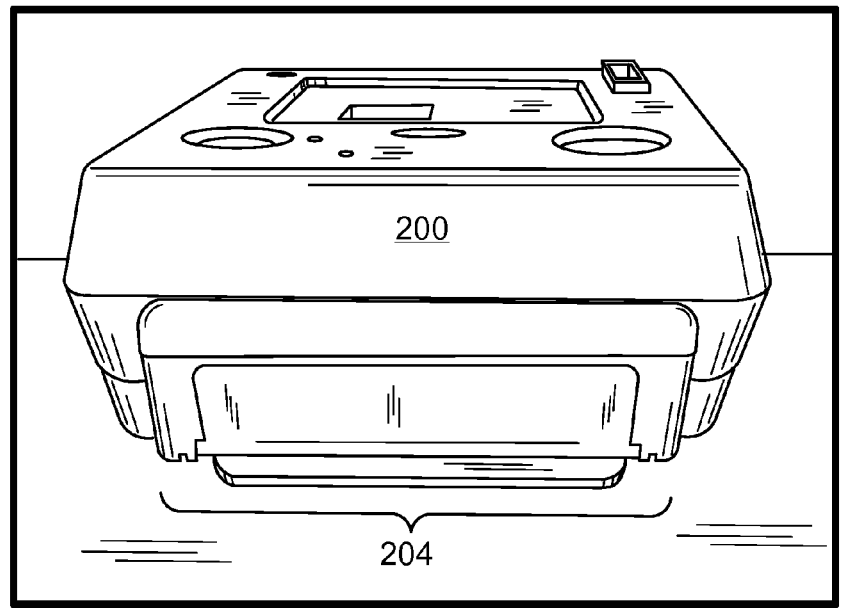
Figure 2D:
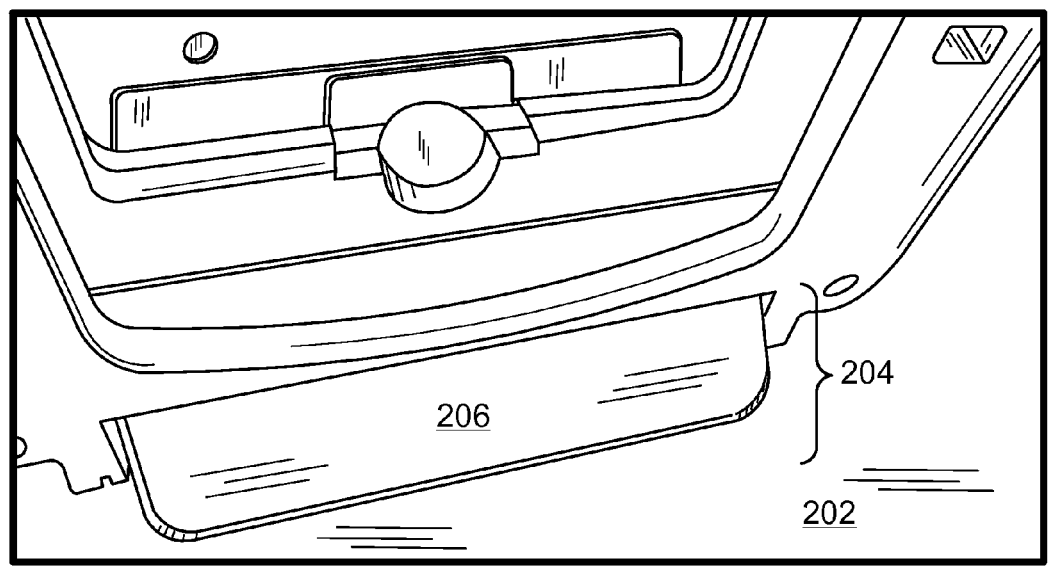

FIG. 1 presents an AED 100 located in an accessible wall cabinet 102. The AED 100 may be any type of automated external defibrillator from any manufacturer that is capable of being positioned in the accessible wall cabinet 102. For example, AED 100 may be the AED Plus II®, AED Plus® or AED Pro® manufactured by ZOLL Medical Corporation of Chelmsford, Mass. The volume that contains the AED 100 within the wall cabinet 102 can generally be considered as having a rectangular box shape; however, other the storage volume shapes may be employed. In this example, the body shape of the AED 100 generally conforms to this shape of the cabinet's interior. As such, the body of the AED 100 can be considered as having a rectangular box shape. While such a conforming shape may be easily receivable by the container, this shape of the AED 100 may present disadvantages when removed for use. For example, removed from the wall cabinet 102 and deployed at an emergency scene (e.g., positioned next to a victim on a floor, the AED 100 may topple over since the device is taller (in the vertical direction) than being long or wide (in either horizontal direction). When stowed, sidewalls of the wall cabinet 102 assist to maintain the AED 100 upright, however, when deployed external from the cabinet the sidewalls can no longer help the AED remain upright. Such stability issues may become exacerbated if the AED 100 needs to be deployed in less than optimum conditions (e.g., an uneven surface, a slick surface, harsh weather conditions, etc.). Further, presentation of information by the AED 100 (e.g., from one or more incorporated displays) may be hindered if the AED is unable to maintain its operational position while a patient is being treated at an emergency situation.

FIG. 2(*a*)-(*c*) presents a support mechanism that is incorporated into an AED to assist maintaining the deployed position of the AED. As illustrated in FIG. 2(*a*), an AED 200 has been removed from being stowed in a wall container or other type of container (e.g., a shipping box, storage container, etc.) and stands substantially upright on a surface 202. In this example, the AED is positioned off from vertical (e.g., 5°, 10°, 20°, etc.) due to a tilt provided by the support mechanism. Along with improving the positional stability, the introduced tilt may assist emergency personnel with viewing the information being presented by the AED 200.

To improve the upright positional stability of the AED 200, one or more techniques may be employed by the support mechanism. Referring to FIG. 2(*b*), a support mechanism 204 is incorporated into the lower back portion of the AED 200. In this example, the support mechanism 204 is connected to the AED 200 and engages a portion of the surface 202 upon which the AED 200 rests upon. Along with assisting with supporting the AED 200, the support mechanism 204 is also moveable for attaining multiple positions (e.g., a deployed position, a stowed position, etc.). With this capability, the support mechanism 204 may be placed into a stowed position to allow the AED 200 to conform to the shape of the storage volume of a container (e.g., the wall container 102) and be placed into a position to help stabilize the AED 200 when deployed. The support mechanism 204 may also be placed in a stowed position based upon other conditions. For example, when laid upon its back (e.g., so the display of the AED 200 is presented upward to a viewer), the weight of the AED produces a force that causes the support mechanism 204 to retract and be placed in a stowed position.

The support mechanism 204 may include one or more members for performing these capabilities, for example, one or more stands may be connected to the AED 200 for engaging a variety of surface types. Further the shape, form, etc., of the support mechanism (or the included members) may be designed for providing such capabilities. For example, a support member may include telescoping portions that extend to stabilize the position of the AED and retract to conform to a container volume.

One or more connection techniques may also be utilized for securing the support mechanism 204 to the AED 200. For example, one or more hinges may be included in the support mechanism for connecting to the AED 200.

In some arrangements, the support mechanism may be placed into one position due to one or more forces experienced by the support mechanism. For example, the support mechanism may normally be held in one position (e.g., a deployed position) and an applied force is needed move the support mechanism into another position (e.g., a stowed position). Being naturally held in the deployed position, the support mechanism 204 may be designed to automatically return to this position if the force holding it in another position is released. For example, due to the interior shape of a container (e.g., the wall cabinet 102) a sidewall of the container may exert a force and hold the support mechanism of the AED in a stowed position. Upon removing the AED from the container, the force provided by the sidewall would be released and the support mechanism is allowed to return to its nature position (e.g., a deployed position). Such a force may also be provided by the AED itself. For example, as shown in FIG. 2(*c*), placed on its back, the weight of the AED 200 causes a force to be produced that retracts the support mechanism 204 and places it into a stowed position. Lifting the AED off of its back (e.g., for upright placement), the support mechanism would return to its deployed position. One or more type of techniques may be employed for holding a support mechanism in one position (e.g., a deployed position) until a force is applied to place the support mechanism in another position (e.g., a stowed position). For example, one or more springs may be included in the support mechanism (e.g., a spring loaded hinge) that produce a force for holding the mechanism in one position (e.g., a deployed position). Similar to the use of one or more springs, other force providing mechanism may be employed.

For one possible arrangement, FIG. 2(*d*) shows a mechanical stand 206 included in the support mechanism 204, which can assist the supporting of the AED 200 to maintain its upright position. In this example, the stand 206 extends from the lower back portion of the AED 200 such that a predefined angle is formed between the surface 202 and the AED. In some arrangements, this angle may be adjustable by the user or self-adjusted by the spring (e.g., for different types of surfaces, terrains, etc.). Alternatively, the angle may be fixed by the manufacturer for some types of AEDs.

Figure 3A:
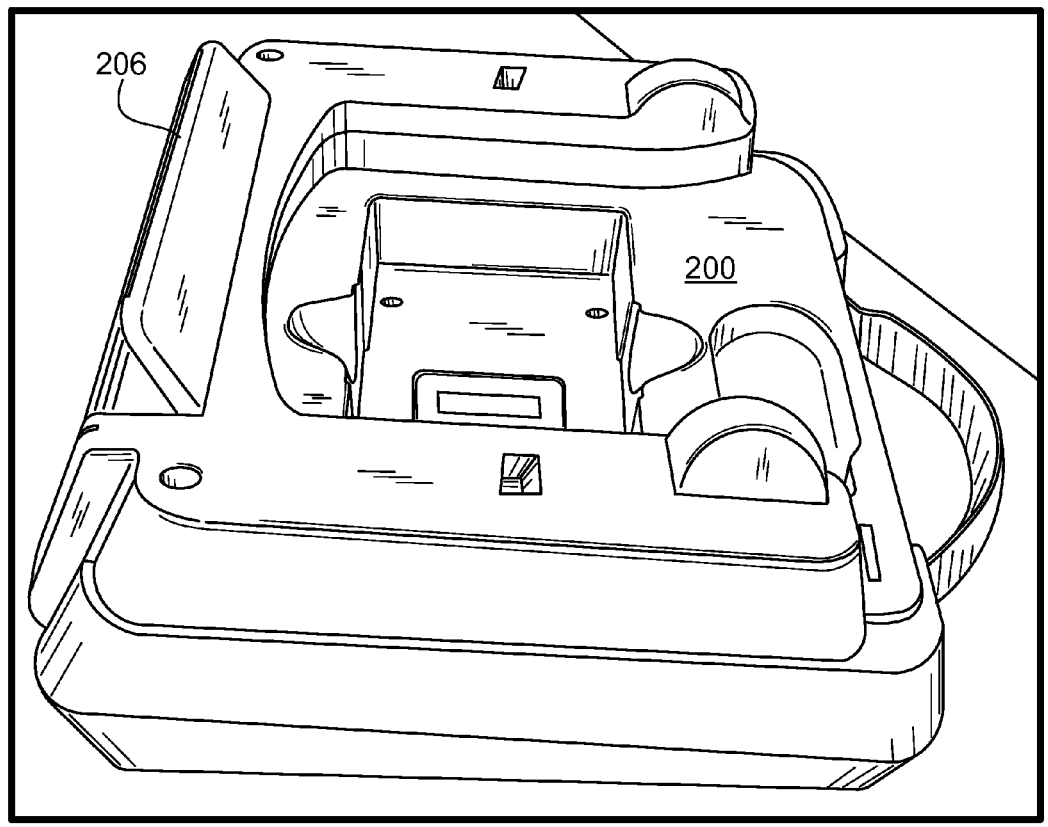
FIG. 3(a)-(c) illustrates the deployment and stowed position of the AED stand.
Figure 3B:
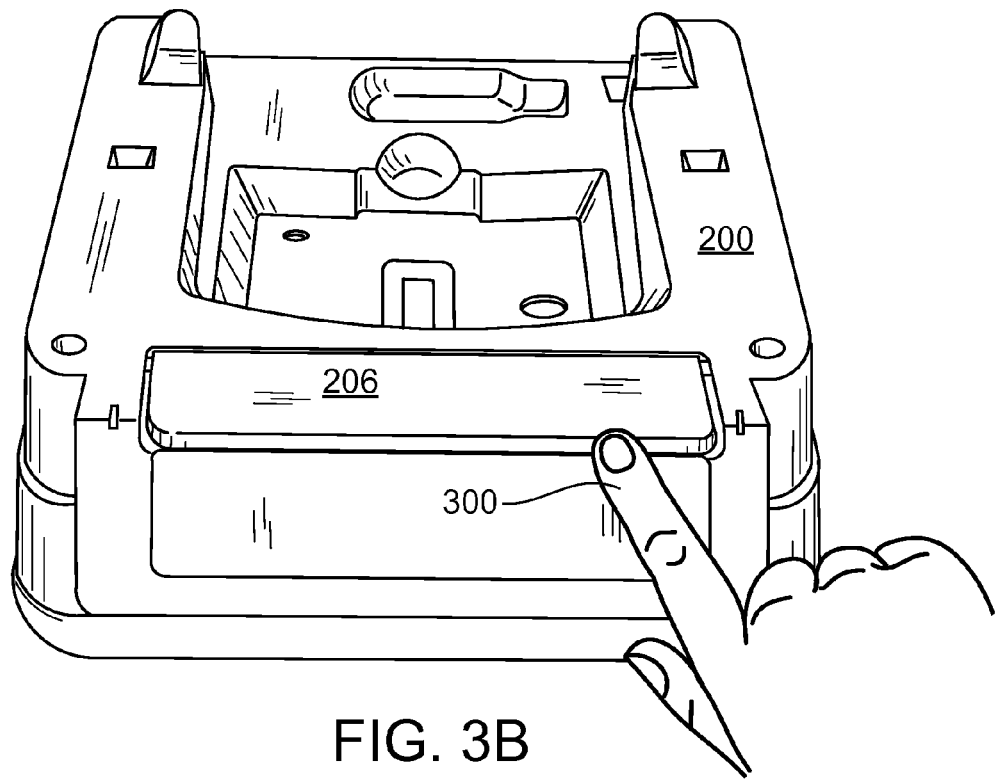

Referring to FIG. 3(*a*)-(*c*) a series of images are shown in which the AED 200 has been positioned face down to demonstrate the angular range of a support mechanism. FIG. 3(*a*) presents a side view of the AED 200 lying face down on a surface. Similar to FIG. 2(*c*), the support mechanism includes the stand 206, although multiple stands or different types of support members may be included in the support mechanism and utilized. In FIG. 3(*a*), the stand 206 is in a deployed position and an angle is formed between the stand and the AED 200. In this example, a spring is used in concert with a hinge (e.g., a spring loaded hinge) to position and hold the stand 206 in the deployed position absent any force being applied external from the AED 200.

In FIG. 3(*b*), the image of the AED 200 has been rotated 90° (to provide another viewing perspective) and a finger 300 is shown applying an external force to the end of the stand 206, thereby causing the stand to be placed into another position. As illustrated, the stand 206 is moved in a downward direction and is placed in a stowed position. Generally, the angle between the stand 206 and the AED 200 is reduced or even eliminated (e.g., the angle is reduced to 0°) by applying the force. The inner sidewall of a container (e.g., the wall container 102) may apply a similar force to the stand 206 and reduce the angle between the stand and the AED such that the stowed AED better conforms to the shape of the inner volume of the container. Similarly, with brief reference to FIG. 2(c), placed upon its back, the weight of the AED 200 may cause a force that reduces or eliminates the angle and places (e.g., retracts) the stand 206 into a stowed position.

Figure 3C:
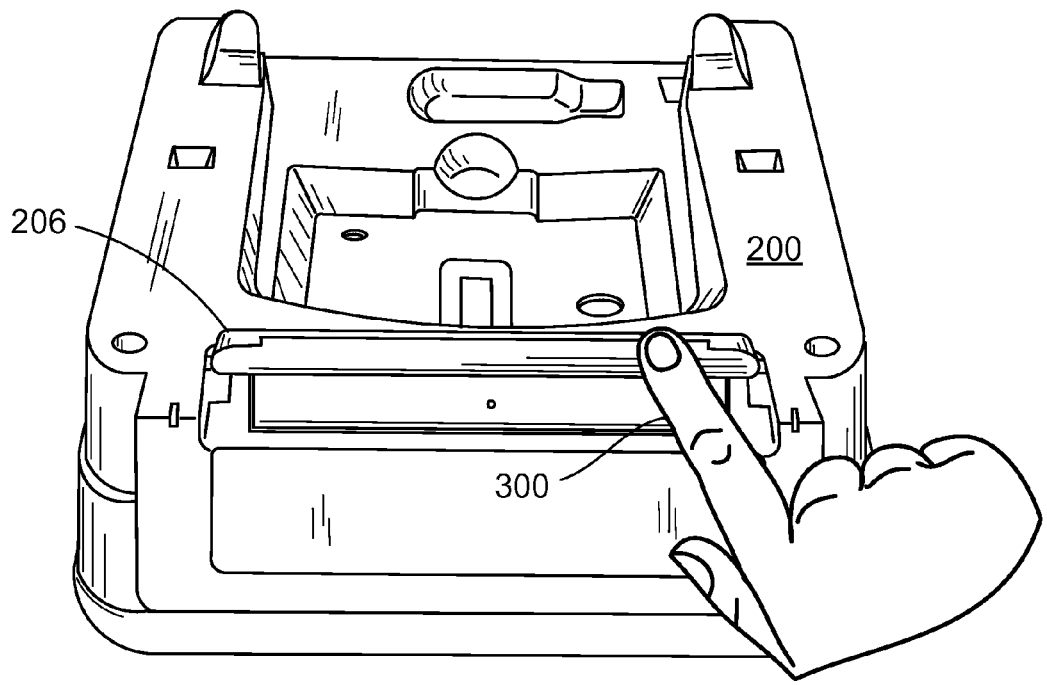

Once the external force is removed, energy stored in the spring-loaded hinge (connecting the stand 206 and the AED 200) returns that stand to the deployed position by expanding the angle between the stand and the AED. As illustrated in FIG. 3(c), the force applied by the finger 300 is reduced and the stand 206 returns to its deployed position and the angle between the stand and AED 200 returns to its pre-defined value. As such, if the AED 200 is removed from a container (e.g., the wall container 102), the force applied by a sidewall is removed and the stand 206 relatively quickly moves into its deployed position. As such, an emergency professional can remove the AED 200 from a container and place the device in an upright and stable position on various types of surfaces. Further based upon the angular travel allowed by the spring-loaded hinge, the angle between the stand 206 and the rest of the AED 200 can adjust to the contour of the surface without excessive focus from the emergency professional.

In some arrangements, the support mechanism may provide other functionality. For example, operations of the AED may depend upon the position of the support mechanism, for example, the AED may not operate (e.g., turn on) unless the support mechanism is in a proper position (e.g., deployed, stowed, etc.).

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes example embodiments of the invention, these descriptions should not be viewed in a limiting sense. Rather, there are several variations and modifications which may be made without departing from the scope of the present invention as defined in the appended claims.

What is claimed is:

1. An apparatus, comprising:
    an automated external defibrillator including at least one display; and
    a support mechanism for supporting the automated external defibrillator, the support mechanism includes a stand connected to a hinge that is connected to the automated external defibrillator, wherein the hinge is capable of placing the stand in a deployed position for supporting the automated external defibrillator during operation and is capable of placing the stand in a stowed position for storing the automated external defibrillator,
    wherein the hinge automatically places the stand in the stowed position when the apparatus is placed in a first orientation, and
    wherein the hinge automatically places the stand in the deployed position when the apparatus is placed in a second orientation, such that the stand supports the apparatus in the second orientation.

2. The apparatus of claim 1, wherein a first angle is formed between the stand and the automated external defibrillator when in the deployed position.

3. The apparatus of claim 2, wherein a second angle is formed between the stand and the automated external defibrillator when in the stowed position.

4. The apparatus of claim 3, wherein the first angle is larger than the second angle.

5. The apparatus of claim 1, wherein the hinge places the stand in the deployed position absent an external force being applied to the stand.

6. The apparatus of claim 1, wherein the hinge places the stand in the stowed position when an external force is applied to the stand.

7. The apparatus of claim 6, wherein the stand is configured to receive the external force from a portion of a storage container.

8. The apparatus of claim 1, wherein the hinge is spring loaded and places the stand in the deployed position absent an external forces being applied to the stand.

9. The apparatus of claim 1, wherein the hinge is spring-loaded and places the stand in the stowed position when an external force is applied to the stand.

10. The apparatus of claim 1, wherein the hinge is spring-loaded and places the stand in the stowed position when the apparatus is placed on its back.

11. The apparatus of claim 1, wherein in the first orientation, the apparatus rests with a first portion against a supporting surface, and
    wherein in the second orientation, the apparatus rests with a second portion against the supporting surface.

12. The apparatus of claim 1, wherein the stand extends from a rear surface of the apparatus, and
    wherein when the apparatus is placed with its rear surface against a support surface, a weight of the apparatus places stand in the stowed position, and when the apparatus rests its rear surface away from the supporting surface, the hinge automatically places the stand in the deployed position.

13. An apparatus, comprising:
    an automated external defibrillator including at least one display; and
    a support mechanism for supporting the automated external defibrillator, comprising:
        a stand capable of assisting the supporting of the automated external defibrillator during operation, and
        a spring-loaded hinge that is connected to the stand and the automated external defibrillator, the spring-loaded hinge is capable of placing the stand in a deployed position for supporting the automated external defibrillator during operation and is also capable of placing the stand in a stowed position for storing the automated external defibrillator;
    wherein the spring-loaded hinge places the stand in the deployed position absent an external force being applied to the stand,
    wherein the spring-loaded hinge automatically places the stand in the stowed position when the apparatus is placed in a first orientation, and wherein the hinge automatically places the stand in the deployed position when the apparatus is placed in a second orientation, such that the stand supports the apparatus in the second orientation.

14. The apparatus of claim 13, wherein a first angle is formed between the stand and the automated external defibrillator when in the deployed position.

15. The apparatus of claim 14, wherein a second angle is formed between the stand and the automated external defibrillator when in the stowed position.

16. The apparatus of claim 15, wherein the first angle is larger than the second angle.

17. The apparatus of claim 13, wherein the spring-loaded hinge places the stand in the stowed position when the apparatus is placed on its back.

18. The apparatus of claim 11, wherein the hinge biases the stand towards the deployed position, and
wherein when the apparatus is in the first orientation, a weight of the apparatus places stand in the stowed position, and when the apparatus is in the second orientation, the hinge automatically places the stand in the deployed position.

\* \* \* \* \*